US006432716B2

(12) United States Patent
Winograd et al.

(10) Patent No.: US 6,432,716 B2
(45) Date of Patent: Aug. 13, 2002

(54) METHOD TO IDENTIFY A SURFACE-BOUND MOLECULE

(75) Inventors: Nicholas Winograd, Spring Mills, PA (US); Donald E. Riederer, Columbia, MO (US); Reema Chatterjee, St. Paul, MN (US)

(73) Assignee: The Penn State Research Foundation

( * ) Notice: Subject to any disclaimer, the term of this patent is extended or adjusted under 35 U.S.C. 154(b) by 0 days.

(21) Appl. No.: 09/051,216

(22) PCT Filed: Oct. 3, 1996

(86) PCT No.: PCT/US96/15991

§ 371 (c)(1),
(2), (4) Date: Dec. 18, 1998

(87) PCT Pub. No.: WO97/12897

PCT Pub. Date: Apr. 10, 1997

Related U.S. Application Data

(60) Provisional application No. 60/004,702, filed on Oct. 3, 1995.

(51) Int. Cl.[7] .......................... G01N 33/00; G01N 33/48

(52) U.S. Cl. ............................... 436/89; 435/6; 436/86; 436/87; 436/88; 436/90; 436/173

(58) Field of Search ............................ 436/86–90, 173; 435/6

(56) References Cited

U.S. PATENT DOCUMENTS 5,539,084 A * 7/1996 Geysen ........................ 530/334
5,547,835 A * 8/1996 Koster ........................... 435/6

FOREIGN PATENT DOCUMENTS

WO 95/25737 * 9/1995

OTHER PUBLICATIONS

R. D. Macfarlane J. Trace Microprobe Tech. 1985, 2, 267–290.*
E. A. Schweikert et al, J. Trace Microprobe Tech. 1987, 5, 1–22.*
J. E. Hunt Nucl. Instrum. Methods Phys. Res. 1987, B27, 181–187.*
D. Griffin et al, Biomed. Environ. Mass Spectrom. 1988, 17, 105–111.*
W. T. Moore et al, Tech. Protein Chem. II, 4th 1991, 511–528.*
Y. Hoppilliard et al, J. Chim. Phys. Phys.–Chim. Biol. 1993, 90, 1367–1398.*
S. C. Story et al, Int. J. Pepetide, Protein Res. 1992, 32, 87–92.*
B. Calas et al, Biomed. Mass Spectrom. 1980, 7, 288–293, Jul. 1980.*
B. J. Garrison et al, Science 1982, 216, 805–812, May 1982.*
T. R. Hayes et al, Springer Ser. Chem. Phys. 1986, 44, 66–68.*
I. Amster et al, Anal. Chem. 1987, 59, 313–317, Jan. 1987.*
S. K. Chowdhury et al, Anal. Biochem. 1989, 180, 387–395.*

(List continued on next page.)

*Primary Examiner*—Arlen Soderquist
(74) *Attorney, Agent, or Firm*—Akerman Senterfitt; Stanley A. Kim

(57) ABSTRACT

The present invention relates to a method of identifying a molecule of a molecule-substrate complex, wherein the molecule is covalently attached directly to a substrate or indirectly by means of a linking moiety, comprising: (a) bombarding the molecule-substrate complex with energized particles to cleave the molecule from the molecule-substrate complex; and (b) determining the molecular weight of the cleaved molecule by means of mass spectrometry. The inventive method may further comprise irradiating the cleaved molecule with photons.

7 Claims, 3 Drawing Sheets

OTHER PUBLICATIONS

N. Winograd et al, Proc. SPIE 1991, 1435, 2–11.*
D. M. Bunk et al, J. Am. Soc. Mass Spectrom. 1991, 2, 379–386, May 1991.*
M. H. Ervin et al, Inst. Phys. Conf. Ser. 1991, 114, 417–420.*
P. A. Van Veelen et al. Rapid Commun. Mass Spectrom. 1991, 5, 565–568, Nov. 1991.*
D. M. Hrubowchak et al, Anal. Chem. 1991, 63, 1947–1953, Sep. 1991.*
M. H. Ervin et al, Surf. Interface Anal. 1994, 21, 298–303.*
C. L. Brummel et al, Science 1994, 264, 399–402, Apr. 1994.*
M. Wood et al, Anal. Chem. 1994, 66, 2425–2432, Aug. 1994.*
R. S. Youngquist et al, J. Am. Chem. Soc. 1995, 117, 3900–3906.*
Nuzzo, "Fundamental Studies of the Chemisorption of Organosulf Compounds on Au(111). Implications for Molecular Self–Assembly on Gold Surfaces," J. Am. Chem. Soc., American Chemical Society, p. 733–740, (Apr. 16, 1987).
Brenner, "Encoded Combinatorial Chemistry," Chemistry, Proc. Natl. Acad. Sci. USA, p. 5381–5383, (Jun. 16, 1992).
Keenan, "Potent Nonpeptide Angiotensin II Receptor Antagonists. 2.," J. Medicinal Chemistry, American Chemical Society, vol. 36 (No. 13), p. 1880–1892, (Apr. 16, 1993).
Weinstock, "Potent and Selective Angiotensin II Receptor Antagonists," J. Medicinal Chemistry, American Chemical Society, vol. 34, (No. 4), p. 1514–1517, (Apr. 16, 1991).
Bunin, "A General and Expedient Method for the Solid-Phase Synthesis of 1,4–Benzodiazepine Derivatives," J. Am. Chem. Soc., American Chemical Society, p. 10997–10998 (Apr. 16, 1992).
Steffens, "A time–of–flight mass spectrometer for static SIMS applications," J. Vac. Sci. Technol., American Vacuum Society, vol. 3 (No. 3), p. 1322–1325, (Jun. 16, 1985).
Poppe–Schriemer, "Sequencing an "unknown" peptide by time–of flight secondary ion mass spectrometry," International J. of Mass Spectrometry and Ion Processes, Elsevier Science Publishers (Amsterdam), p. 301–315, (Apr. 16, 1991).
Rakshit, "A drift–chamber mass spectrometric study of the interaction of H3 ions with neutral molecules at 300K," International J. of Mass Spectrometry and Ion Physics, Elsevier Science Publishers (Amsterdam), p. 185–197, (Apr. 16, 1982).
Benninghoven, "Surface MS: Probing Real–World Samples," Analytical Chemistry, American Chemical Society, vol. 65 (No. 14), p. 630–639, (Apr. 16, 1993).
Lam, "A new type of synthetic peptide library for identifying ligand–binding activity," Nature, vol. 354 (No. 7), p. 82–84, (Nov. 16, 1991).

* cited by examiner

1. WANG RESIN - SB 218303

2. NITRO MERRIFIELD RESIN - SB 220126

3. THIOACETAL RESIN - SB 220127

4. ACETAL RESIN - SB 220128

5. SASRIN RESIN - SB 220261

METHOD TO IDENTIFY A SURFACE-BOUND MOLECULE

The present invention claims benefit of U.S. Provisional Application No. 60/004,702, filed Oct. 3, 1995.

This invention was made with U.S. Government support under Contract No. CHE-9115011. The U.S. Government has certain rights in this invention.

The present invention relates to the field of biophysical analysis of molecules. In particular, the present invention is useful for the identification and analysis of a molecule, such as a member of a combinatorial library, wherein the identified molecule has a demonstrated pharmacological or physiological activity.

Over the past ten years, there has been a growing demand for the production and identification of molecules that have pharmacological or other physiological activity as, for example, agonists or antagonists of various cellular acceptor molecules, such as cell-surface receptors, enzymes, or antibodies. Such molecules can be peptides, oligonucleotides, or other organic compounds, such as heterocyclics and the like, which are commonly the products of combinatorial synthesis, thus forming the members of combinatorial libraries. The unifying feature of these molecules is operational in that they bind specifically to known acceptors. In consequence of such binding, a physiological response occurs whereby certain biological processes are modulated, which can have applications in medicine and agriculture.

Searching for molecules that are useful in medical or veterinary applications, or in agriculture or agrobiology, entails (1) generating collections of such molecules, (2) screening such molecules for physiological activity, and (3) identifying the structure of molecules that provide a positive result in the screen. The first two steps can be accomplished using methods well-known in the art, some of which were discussed in Benkovic et al., PCT/US95/03355, which is incorporated herein in toto by reference. The subject matter of Benkovic et al. related to a mass spectrometric method for identification of such molecules, including those that are members of a combinatorial library. Covalent attachment of such molecules to a substrate, such as a polystyrene or other resins particle, via a suitable linker, thus forming a molecule-substrate complex, is commonly used for purposes of manipulating the molecules; however, for mass spectrometric identification of the molecules, the molecules must be separated from the substrate. One approach that has been used requires use of a photo- or acid-labile linker, however such an approach requires identification of linkers that include either a photo-labile or an acid-labile linkage and subjecting the substrate-attached molecules to a suitable wavelength of light or acid. Such a step requires extra manipulation of the samples, and consumes time. Secondly, the process used to cleave the covalent linkage between the molecule and the molecule-substrate complex may destroy or damage the substrate or the entire molecule-substrate complex, thus retesting of a given molecule requires having additional molecule-substrate complexes.

Accordingly, the analysis of a molecule covalently linked to a substrate, such as the molecules of a combinatorial library, or any collection of molecules so linked to a substrate or substrates, is necessarily impeded by the rate at which substrates, such as beads, having individual molecules attached thereto can be analyzed for the identity of the attached molecule. In view of the literally millions of candidate molecules to be screened in a given library, for example, it is probable that at least hundreds, if not thousands, of the molecule-attached beads would generate positive signals (including false positive signals) requiring further analysis. The limitation of being able to sequence only a few molecules per day, as has been reported by Lam et al., *Nature,* 354, 82 (1991), for example, therefore, presents a strong drawback to current strategies of screening collections of molecules, such as combinatorial libraries, for pharmaceutical compounds. Moreover, if a method allowed identification of a molecule included on a molecule-substrate complex with respect to molecular weight, more preferably with respect to structure, where the molecule was indicated in a screen as having a desireable characteristic, without having to remove such a molecule-substrate complex from the group of other such complexes, in the presence of which the molecule-substrate complex was screened, the procedure of screening and identifying molecules of interest would be greatly improved. Further yet, if a method required essentially a unified step of testing a molecule-substrate complex directly without causing damage to the complex but for the removal of a portion of the included molecule, the process would not only be faster, but would preserve the molecule-substrate complex having a then reduced amount of the molecule, which could be used for further analysis.

SUMMARY OF THE INVENTION

It has now been discovered that a mass spectrometric assay can be used to analyze molecules covalently attached to a substrate, such molecules being peptides, oligonucleotides, heterocyclic molecules, or other chemical species. Such molecules can be members of any collection of molecules including those isolated from natural sources or synthesized, such as those of a combinatorial library. Individual members of a collection of molecules, for example, can be constructed on or attached to a suitable substrate or substrates and screened, and the individual substrate or portion thereof that is identified as having a molecule that, for example, specifically interacts with an acceptor molecule of interest (i.e., positive screen result) can be identified in the presence of identical substrates having other unselected molecules attached thereto and subjected to mass spectrometric assay without removal from the total collection to determine the precise molecular weight of the selected molecule. A preferred aspect of the method includes the use of linking moieties or substrates having reactive groups attached thereto that covalently link the individual molecules of the collection to the substrate, whereby the linkage of at least a portion of the molecules linked to the substrate is cleaved without disturbing the molecule's structure or the integrity of the substrate, allowing analysis of the free molecules and subsequent analysis of the remaining linked molecules. Consequently, the present invention greatly improves the ability of artisans of the relevant art to identify, for example, pharmaceutically active agents derived from collections of molecules, such as combinatorial libraries.

In particular, the present invention relates to a method of identifying a molecule of a molecule-substrate complex, wherein the molecule is covalently attached directly to a substrate or indirectly by means of a linking moiety, comprising:

(a) bombarding the molecule-substrate complex with energized particles to cleave the molecule from the molecule-substrate complex; and (b) determining the molecular weight of the cleaved molecule by means of mass spectrometry. Preferably, the method further comprises irradiating the cleaved molecule with photons.

The present method is further directed to a molecule that is selected from the group consisting of amino acids, peptides, oligonucleotides, heterocyclic compounds, and combinations thereof. The substrate used in the context of the present invention preferably comprises a polymeric resin or a metal; and, in another embodiment, further comprises a linking moiety attached thereto. Preferably, the polymeric resin is a polystyrene resin having a linking moiety attached thereto.

The linking moiety used in the context of the present invention preferably comprises at least one reactive group that is selected from the group consisting of hydroxyl, amino, carboxyl, acetal, thioacetal, $C_1$–$C_{10}$ alkylamino, $C_1$–$C_{10}$ aralkylamino, and $C_1$–$C_{10}$ haloalkyl, and an o-nitrobenzylic group having a benzylic hydrogen. Preferably, the linking moiety is selected from the group consisting of F-moc-2,4-dimethoxy-4'-(carboxymethyloxy)-benzhydrylamine, F-moc-methoxy-4'(gamma-carboxypropyloxy)benzhydrylamine, p-alkoxybenzyl alcohol, benzylacetal, benzylthioacetal, benzhydrylamine, Cl—$CH_2$-Ph, 2-methoxy-4-alkoxy benzyl alcohol, and o-nitrobenzyloxy carbonyl. More preferably, the linking moiety is selected from the group consisting of 2-methoxy-4-alkoxy benzyl alcohol, benzylacetal, and benzylthioacetal.

The present method includes cleaving the molecule from the substrate in the molecule-substrate complex without substantial modification of the molecule or destruction of the substrate. Such cleaving is preferably accomplished by bombardment of the molecule-substrate complex with energized particles, wherein the particles are preferably gallium or argon. The particles are energized by subjection to an electric field of between about one and about 30 kilovolts. It is believed that the free molecule that results from the bombardment is charged or uncharged; the molecule becomes charged or further charged by irradiation by a laser beam.

The substrate used in the context of the present method is preferably a bead. A bead used in this context has a diameter of from about 10 microns to about 120 microns.

The mass spectrometry used in the present invention is preferably time-of-flight secondary ion mass spectrometry. The method further comprises mapping of the spatial distribution of the molecules on the aforementioned beads that, for example, are arranged on a grid.

In a preferred embodiment, the molecule subjected to analysis under the present invention is an amino acid or a peptide. Preferably, the peptide comprises two to ten amino acids. The method further comprises determination of the sequence of the peptide from the fragmentation pattern obtained in the mass spectrometry. Alternatively, the molecule subjected to analysis under the present invention is a heterocyclic compound comprising four to seven membered rings having N, S, or O, and combinations thereof.

A preferred embodiment of the present invention relates to a method of identifying a molecule of a molecule-substrate complex, wherein the molecule is covalently attached directly to a substrate or indirectly by means of a linking moiety, comprising:

(a) bombarding the molecule-substrate complex with energized particles to cleave the molecule from the molecule-substrate complex;

(b) irradiating the cleaved molecule with photons; and (c) determining the molecular weight of the irradiated molecule by means of mass spectrometry, wherein the substrate is a polystyrene bead having a reactive group, the molecule is an amino acid, peptide, oligonucleotide, or a heterocyclic compound, or a combination thereof, the covalent bond is sensitive to energized particle bombardment, the energized particles are gallium atoms, the photon source is a laser, and the mass spectrometry is time-of-flight secondary ion mass spectrometry.

These and other features and advantages of the invention will be more readily apparent upon reading the following detailed description of the invention and upon reference to the accompanying drawings, all of which are given by way of illustration only, and are not limitative of the present invention.

DETAILED DESCRIPTION

Figure 1:
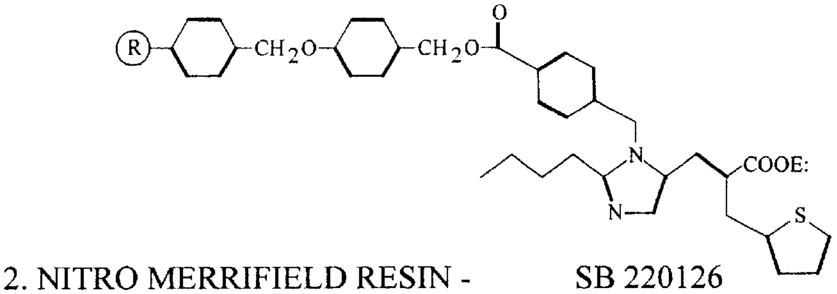
FIG. 1 depicts various linking moieties attaching angiotensin II receptor antagonist to various polystyrene substrates.
Figure 1:
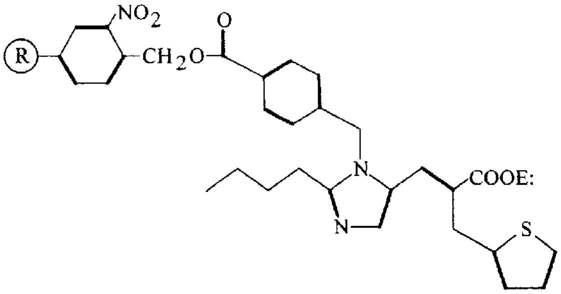
Figure 1:
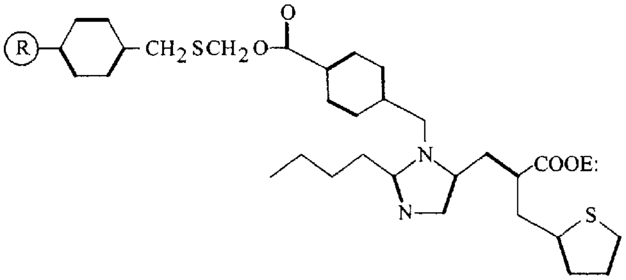
Figure 1:
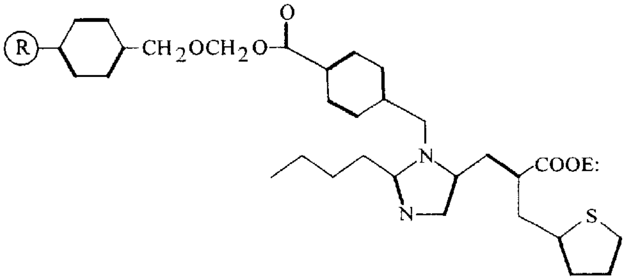
Figure 1:
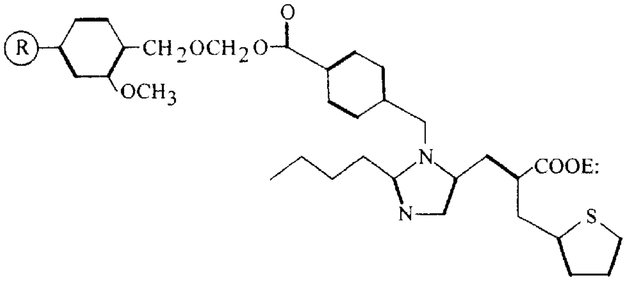

The following detailed description of the instant invention is provided to aid those skilled in the art in practicing the present invention, but should not be construed to limit the present invention, as modifications and variations in the embodiments herein discussed may be made by those of ordinary skill in the art without departing from the spirit or scope of the present inventive discovery.

The following terms shall have the definitions provided herewith:

collection—a set of molecules, which may be present as molecule-substrate complexes, such as a combinatorial library, but not limited thereto.

linker—a linking moiety used for indirect attachment of a molecule to a substrate, or the functional group used for direct attachment of a molecule to a substrate.

linking moiety—a chemical unit that is covalently attached to the molecule and attached to the substrate.

linking substrate—a substrate comprising a reactive group to which a molecule can attach covalently thereto.

molecule—a chemical unit composed of one or more atoms, which may or may not be charged.

molecule-substrate complex—a substrate having a molecule covalently attached thereto, either directly via a functional group on the substrate or indirectly via a linking moiety.

substrate—a surface to which a molecule can be attached, either directly by a reactive group included with the substrate, as in a linking substrate, or indirectly by a linking moiety.

The present invention provides a method used in the inventive method that greatly improves the ability of an ordinary artisan to identify and characterize a molecule that is attached to a surface. Molecules of particular interest that can be identified in the context of the present invention include amino acids, peptides, oligonucleotides, heterocyclic compounds, combinations thereof, and the like. Such molecules include, in particular, pharmaceutically-active molecules, which can be members of collections of synthesized molecules or isolated natural molecules. Synthetic molecules include those prepared by combinatorial chemical methods known to the art, which collections are commonly referred to as combinatorial libraries. The members of such a collection can be constructed in association with or attached to a suitable substrate, such as a polystyrene bead surface. Such association between the molecules and the substrates, referred to herein as molecule-substrate complexes, are preferably mediated by covalent linkage, particularly during the construction of combinatorial libraries, for example. Preferably, the covalent linkage is cleaved using means that does not modify or substantially modify the structure of the linked molecule, nor does the means modify or substantially modify the substrate. A molecule or substrate that is not substantially modified by the cleavage of the molecule from the molecule-substrate complex has, with respect to the molecule, a molecular weight as measured by mass spectrometry that provides sufficient information such that the molecular weight of the molecule on the substrate can be deduced, i.e., positive results, and with respect to the substrate, retains a sufficient quantity of attached molecules such that a subsequent mass spectrometric run directed at the molecule-substrate complex would provide positive results.

Molecules from any of the aforementioned collections preferably are provided as molecule-substrate complexes, as discussed herein. The linker used to form the molecule-substrate complexes must be selected for linkers that provide a covalent linkage to the molecule that will preferentially be cleaved by the ion beam of the mass spectrometric method of the present invention. By preferential cleavage of the linker, it is intended that at least about 5% of the cleavage events caused by the ion beam occur at a covalent bond or bonds within the linker or between the linker and the molecule. Prefered linkers are associated with preferential cleavage of at least about 20%. More prefered linkers are associated with preferential cleavage of at least about 50%.

The molecules of a preferred collection are linked covalently to the substrate, using methods well known in the art, thus forming a molecule-substrate complex. A preferred covalent linkage between the molecule and the substrate has the characteristic of being able to break in response to external changes caused by energized particles at levels that do not modify or do not substantially modify the structure of the molecules or the substrates of the collection. Such a covalent linkage may be effected, for example, by means of a suitable linking moiety that couples both to the molecule and the substrate. The substrate itself can include suitable reactive groups coupled thereto, such that such a linking substrate links to a molecule without need of a separate linking moiety. Examples of such linking substrates are included in FIG. 1. When a linking moiety or a linking substrate is used, the covalent bonds between the molecule and the substrate will break in consequence of the energized particles at one or more of the covalent bonds associated with the linking moiety or the aforementioned reactive groups of the linking substrate, thereby destroying any covalent linkage between the molecule and the substrate. At least an appreciable proportion of the population of molecules will be fully free of the covalent linkage, however, some or even a majority of the molecules may remain attached covalently.

As noted above, the covalent linkage is broken by bombarding the molecule-substrate complex with energized particles. Suitable particles include, without limitation, gallium or argon atoms, which are energized by subjection of such or other particles to an electric field between about one and about 30 kilovolts. Such molecules so freed of their covalent linkage to the substrate typically are uncharged. However, in essentially the same step, an uncharged free molecule is ionized by irradiation by a suitable ionization means, such as a laser beam, as discussed herein.

Suitable linking moieties or linking substrates are those that comprise a reactive functional group selected from the group consisting of alcohol, amino, carboxyl, acetal, thioacetal, and aminoalkyl, aralkyl, amino aralkyl, and haloalkyl, and a nitroaromatic group having a benzylic hydrogen ortho to the nitro group, such as o-nitrobenzyl derivatives, and benzylsulfonyl derivatives; and which covalent bond formed with such a group is cleavable by exposure to a suitable energized particle, as discussed above. Preferably, the linking moiety or linking substrate comprises at least one reactive group that is selected from the group consisting of hydroxyl, amino, carboxyl, acetal, thioacetal, $C_1$–$C_{10}$ alkylamino, $C_1$–$C_{10}$ aralkylamino, and $C_1$–$C_{10}$ haloalkyl, and an ortho-nitrobenzylic group having a benzylic hydrogen.

In particular, suitable linking moieties include p-alkoxybenzyl alcohol (used in the Wang resin), F-moc-2,4-dimethoxy-4'-(carboxymethyloxy)-benzhydrylamine, F-moc-4-methoxy-4'-(gamma-carboxypropyloxy)-benzhydrylamine, 4-hydroxymethyl-phenoxy-acetic acid, aminomethyl (used in the PAM resin), benzhydrylamine, Cl—$CH_2$-Ph-(used in Merrifield resin), benzylacetal (used in the Acetal resin), benzylthioacetal (used in the Thioacetal resin), and 2-methoxy-4-alkoxybenzyl alcohol (used in Sasrino® resin). See FIG. 1. Preferred linking moieties include F-moc-2,4-dimethoxy-4'-(carboxymethyloxy)-benzhydrylamine, F-moc-methoxy-4'(gamma-carboxypropyloxy)benzhydrylamine, p-alkoxybenzyl alcohol, benzhydrylamine, $ClCH_2Ph$, 2-methoxy-4-alkoxy benzyl alcohol, 6-nitroveratryloxy carbonyl, 2-nitrobenzyloxycarbonyl, and $\alpha,\alpha$-dimethyl-dimethoxybenzyloxycarbonyl, more preferred linking moieties include 2-methoxy-4-alkoxybenzyl alcohol. It is appreciated that different linker chemistry may enhance the molecular ion signal of covalently attached species.

The covalent linkage between the substrate and the molecule may also be mediated by a reactive group or groups attached to the substrate, as in the aforementioned linking substrate. For example, as recited above, the polystyrene-derivative bead known as Sasrin® (Bachem Biosciences) has a reactive group (2-methoxy-4-alkoxy benzyl alcohol) that covalently couples to carboxylic acid groups found on all peptides. See FIG. 1.

Construction of a combinatorial library or any of the other collections herein noted is known to the art and described elsewhere, such as Benkovic et al., PCT/US95/03355 and Lam et al. (supra), as examples. Screening of such collections is also described in the aforementioned references. A preferred identification approach would take into account the fact that molecule-substrate complexes that include, for example, peptides, oligonucleotides, or heterocyclic compounds can be constructed such that the molecules are desorbed intact or substantially intact from a substrate, particularly from a bead surface, even when covalently attached to the substrate initially. Because each bead, for example, may have adsorbed thereto only a femtomole quantity of a particular molecule, or less, and only a portion of the particular molecule is desorbed in a given analytical run, extreme sensitivity of the method of analysis is required. For example, a standard 40 micron sphere covered with one layer of phenylalanine will only have about 50 femtomoles of surface molecules available for sampling. With sufficient sensitivity of the analytical procedure, and the capability of preserving a given molecule-substrate complex after a portion of the included molecules have been removed, provides a valuable method for analyzing and re-analyzing particular molecules.

The present method measures the molecular weight of such molecules upon their removal from the substrate and subsequent ionization. Removal from the substrate is accomplished by application of a suitable ionic beam, such as one resulting by subjecting gallium or argon, for example, to an electric field of between about one and about 30 kilovolts. If the so removed molecule is uncharged, it becomes charged by passing through a suitable laser beam, as is known in the art. A suitable laser has a pulse length of about 10 nanoseconds or less, a wavelength in the ultraviolet range, and produces energy per pulse of about 1 to about 10 millijoules. Alternatively, if the so removed molecule is charged, the laser is unnecessary, although it may serve to increase the charge on the molecule. The remaining step of the method employs any suitable design of mass spectrometry for determining molecular weight of the ionized molecule.

The method preferably employs imaging secondary ion mass spectrometry to identify the molecular weights of molecules adsorbed to the polystyrene bead surfaces, such as magnetic sector SIMS, quadrupole SIMS, Fourier Transformation SIMS, or time-of-flight SIMS (TOF-SIMS). The methodology actually used for any given SIMS analysis is known in the art, and may vary both with the machine used and artisan operating the machine. Preferably, the present invention employs TOF-SIMS. Detection of the mass of secondary ions formed in a TOF-SIMS protocol allows the unique identification of the corresponding library member, presuming that the method of construction of the library is known so that an artisan can assign discrete molecular weights to all molecules so generated and ionization fragments thereof (generated in the TOF-SIMS method).

In TOF-SIMS, a pulsed beam of primary ions is directed to a sample surface. The arriving primary ions desorb molecules of the sample present in a monolayer at the surface of the sample. Molecules that were attached to the surface by a covalent linkage, for example, and are so desorbed are typically uncharged in that no mass spectrometric profile results in the absence of an ionization means. Such molecules become charged by a suitable ionization means, such as a laser, which is positioned in an instrument by which the present method can be performed such that any such uncharged desorbed molecules become charged. For example, uncharged desorbed molecules, upon receiving thermal energy, can evaporate and immediately migrate into a laser beam, by which they become charged, thus forming secondary ions. These generated secondary ions are then accelerated to a uniform energy by an electric field, and drift through a fixed distance to a detector. The time-of-flight of these uniform energy particles through the fixed distance is directly proportional to the mass-to-charge ratio (m/z) of the ion. Because only the time-of-flight of an ion is measured to determine its mass, TOF-SIMS provides for parallel detection of all masses present in a sample, and an effectively unlimited mass detection range with high mass resolution. Indeed, TOF-SIMS provides a $10^4$–$10^6$ fold improvement in sensitivity over scanning mass spectrometric methods employing other detectors, such as magnetic sector fields and quadrapoles, which are well known in the art. TOF-SIMS thus provides a direct mass spectrometric assay that is generally applicable to reading a wide variety of molecules assembled in a collection, such as a combinatorial library.

The considerations relevant to use of TOF-SIMS for such assays are discussed in the literature. For example, as discussed by Winograd in *Ion Beams and Laser Postionization for Molecule-Specific Imaging* (*Anal. Chem.,* 65, 622A–629A (1993)), an energetic primary ion bombarding a sample on a solid surface creates a large amount of damage within 50 Angstroms of the point of impact. Unless the dose of incident ions is kept below approximately 1% of the number of sample molecules forming a monolayer, the ion bombardment alters the surface chemistry. The dose of incident ions of 1% is referred to as the "static limit." In TOF-SIMS, the dosage of primary ions remains below the static limit because the incident ion beam is directed toward the sample as a very short pulse. Use of a pulsed incident beam is also advantageous because a spectrum with a dynamic range of several orders of magnitude can be obtained by the accumulation of a large number of cycles with high repetition rates, as discussed by Benninghoven et al. in *Surface MS: Probing Real-World Samples* (*Anal. Chem.,* 65, 630A–639A (1993)). Increased sensitivity may also be realized using special cationization schemes or by laser postionization of sputtered neutral molecules, as discussed by Winograd et al., *Inst. Phys. Conf. Ser.,* 128, 259 (1992).

The TOF-SIMS technique also allows the primary ion beam to be focused to a spot size of less than 150 nm, thereby allowing the concentration of molecules to be mapped over spatial domains by rastering or moving the ion beam across pixels defined on the sample and taking spectra at each pixel. Other aspects of TOF-SIMS imaging are discussed by Chait and Standing in *Time-of-Flight Mass Spectrometer for Measurement of Secondary Ion Mass Spectra* (*Int. J. Mass Spectrom. Ion Phys.,* 40, 185–193 (1981)); and by Steffens et al. in *A Time-of-Flight Mass Spectrometer for Static SIMS Applications* (*J. Vac. Sci. Technol., A* 3(3), 1322 (1985)).

In certain situations, the information obtained by TOF-SIMS may not fully distinguish and identify all members of a combinatorial library. For example, various isomers of a given peptide may be present, each having the same mass, as, for example, in the case of phenylalanine-glycine-leucine and glycine-leucine-phenylalanine. In such situations, TOF-SIMS can be used to determine the sequence of the selected peptide nonetheless, provided that the library was constructed from a known set of building blocks. As discussed by Poppe-Schriemer et al. in *Sequencing an "Unknown" Peptide by Time-of-Flight Secondary Ion Mass Spectrometry* (*Int. J. Mass Spectrom. Ion Phys.,* 111, 301–315 (1991)), the parent ions subjected to TOF-SIMS necessarily break down to the various fragment ions, the masses of which can be compared and analyzed based on existing mass data to determine the structure of the selected peptide. This procedure is effective to the extent that the selected molecule is one of the possible peptides of the combinatorial library as determined by the construction of the library. This procedure is also limited by the resolving power of TOF-SIMS to distinguish such fragmentions (TOF-SIMS mass accuracy is currently on the order of ±0.01 amu, according to Winograd, supra).

Alternatively, an isotope indexing scheme can be used to differentiate between molecules that otherwise have the same mass. For example, to differentiate between phenylalanineglycine-leucine and glycine-leucine-phenylalanine, one can either examine the fragmentation pattern in the SIMS spectrum or synthesize one of the peptides using leucine having $^{15}N$, an isotope that is readily distinguished in TOF-SIMS as its atomic mass is increased by one unit. Distinguishing between a leucine and an isoleucine residue, which are isomers, necessarily would require such an alternate method. Similarly, one could use differentially L and D amino acids, using methods well known in the art.

In particular, the present invention relates to a method of identifying a molecule of a molecule-substrate complex, wherein the molecule is covalently attached directly to a substrate or indirectly by means of a linking moiety, comprising: (a) bombarding the molecule-substrate complex with energized particles to cleave the molecule from the molecule-substrate complex; and (b) determining the molecular weight of the cleaved molecule by means of mass spectrometry. Preferably, the mass spectrometry that is utilized in the context of the present invention is TOF-SIMS, as noted above. The molecules can be any suitable molecules, such as, without limitation, at least one of the group consisting of amino acids, peptides, oligonucleotides, or heterocyclic compounds. Such molecules can be synthetic, such as those of a combinatorial library, or isolated from nature. In one embodiment, the present method is applicable to a collection of molecules comprising amino acids that are naturally occurring or synthetic. A preferred collection of molecules is a combinatorial library that has molecules that are peptides or heterocyclic compounds; a more preferred collection of molecules is a combinatorial library that has molecules that are peptides.

Suitable peptides comprise as few as two amino acids to as many as about 50; preferably, suitable peptides comprise from about two amino acids to about 20; most preferably, suitable peptides comprise from about two amino acids to about ten. Any amino acid may be incorporated into peptides screened and identified using the present invention, including any combination of the naturally occurring proteinogenic amino acids as well as amino acids not naturally occurring in proteins such as, but not limited to, dextrorotatory forms of the known amino acids, for example.

Suitable oligonucleotides consist of as few as two nucleotides to as many as about 50; preferably, suitable oligonucleotides consist of from about five nucleotides to about 30; most preferably, suitable oligonucleotides consist of from about five oligonucleotides to about 15. Any nucleotide may be incorporated into an oligonucleotide screened and identified using the present invention, including any combination of the naturally occurring deoxyribonucleotides and ribonucleotides as well as those not naturally occurring in biological systems, such as, but not limited to, H-phosphonate derivatives, N-blocked-5'-O-DMT-deoxynucleoside 3'-(2-cyanoethyl-N,N-diisopropyl) phosphoramidites, N-blocked-5'-O-DMT-deoxynucleoside 3'-(2-cyanoethyl-N,N-diisopropyl)phosphoramidites, N-blocked-5'-O-DMT-deoxynucleoside 3'-(methyl-N,N-diisopropyl)phosphoramidites, N-blocked-5-O-DMT-deoxynucleoside 3'-(2-chlorophenyl)phosphates, N-blocked-5'-O-DMT-deoxynucleoside 3'-(2-chlorophenyl 2-cyanoethyl)phosphate, all of which are nucleoside derivatives used in oligonucleotide synthesis.

Suitable heterocyclic compounds consist of, at minimum, a single three membered ring to as much as a multiple of three membered or greater membered rings coupled by carbon chains of 1 to about 20 atoms in length, such chains being saturated or not. Preferably, suitable heterocyclic compounds include a single three- to seven-membered ring, as well as, but not limited to varying combinations of three-, four-, five-, six-, or seven-membered rings having varying numbers of N, S, or O atoms. More preferably, suitable heterocyclic compounds include benzodiazepine and derivatives thereof (as, for example, disclosed in Bunin et al., *J. Am. Chem. Soc.,* 114, 10997–10998 (1992)), penicillins, cephalosporins, and folate derivatives. most preferred, suitable heterocyclic compounds include benzodiazepine and derivatives thereof, and angiotensin II receptor antagonists. For example, one angiotensin II receptor antagonist that was developed to block the renin-angiotensin system for the treatment of heart failure and possibly chronic renal failure (see, Weinstock et al., *J. Med. Chem.,* 34, 1514 (1991); Keenan et al., *J. Med. Chem.,* 36, 1880 (1993)) can be identified in a mixture of other heterocyclic compounds using the present invention. The formula of the aforementioned angiotensin II receptor antagonist, ethyl 2-(2'-thiophenylmethyl)-3-[5'-{(1'-p-carboxyphenylmethyl)-2'-n-butyl}-imidazolyl]-propenoate, covalently linked to polystyrene beads through various linking moieties is set forth in FIG. 1. The present invention may be applied to the identification of derivatives of such compounds as benzodiazepine and the noted angiotensin II receptor antagonist.

Mixed collections of molecules comprising amino acids, peptides, oligonucleotides, and heterocyclic compounds may be prepared by following standard methods known to one of ordinary skill in the art, such as relates to combinatorial libraries, for example. An oligonucleotide can be, for instance, linked to a peptide through the 5'-hydroxyl of the oligonucleotide. The peptide end can be modified to include a carboxyl group. A process of esterification of the carboxyl group with the 5'-hydroxyl of the oligonucleotide is used to produce a mixed library containing peptide-oligonucleotide molecules. Brenner et al.; (*Proc. Nat'l Acad. Sci. USA,* 89, 5381–5383 (1992) also describes a method of preparation of mixed libraries having nucleotides and peptides. A mixed library comprising a heterocyclic compound and a peptide is also prepared by the reaction of suitable functional groups present on the heterocyclic compound. For instance, the carboxyl group on a heterocyclic compound is reacted with the amino group on the peptide to provide an amide linkage.

The substrate upon or with which the molecules of the combinatorial library are synthesized and/or associated may be any suitable substrate, including, but not limited to, a suitable resin, such as polystyrene, Sasrin®, Wang resin, Pam resin, and Merrifield resin, some of which are set forth in FIG. 1 and are known to the art, and a suitable metal, such as but not limited to gold, further including suitable combinations thereof. Suitable resins or metals are those resins or metals that can covalently attach to a molecule of the aforementioned collections, can be manipulated physically for the purpose of moving the so attached molecules, and can withstand exposure to the ion beam used in the mass spectrometry used in the context of the present invention without becoming substantially damaged. Such resins or metals are commercially available from Bachem Bioscience Inc., for example. The substrate used in the present invention may be formed into any suitable shape, including, but not limited to, spheres, cubes, rectangular prisms, pyramids, cones, ovoids, sheets, and cylinders. Particularly when the substrate is used in the form of a sheet, such as when placed on the surface of a glass microscope slide, defined portions of the sheet may be apportioned for different molecules of a combinatorial library, as disclosed in Fodor et al., supra. Preferably, the substrate as used in the present invention is formed into particles that occupy no more than about 0.0009 $mm^3$, such as a sphere having a diameter of 120 microns, each of which has associated thereto a single molecule structure. More preferred, the substrate used in the present invention is a bead or sphere having a diameter that is from about 10 microns to about 120 microns. Most preferred, the substrate used in the present invention is a bead or sphere having a diameter that is from about 20 microns to about 80 microns.

The following examples further illustrate the present invention and, of course, should not be construed in any way as limiting its scope.

EXAMPLE 1

This example illustrates one embodiment of the present invention wherein a molecular solid covalently linked to a substrate is desorbed from the substrate by bombardment of energized particles resulting in a free uncharged molecule, the resultant free uncharged molecule is ionized by a laser beam, thus forming a secondary ionized particle, and the molecular weight of such a secondary ionized particle is determined by mass spectroscopy.

Self-assembled monolayers (SAMs) were prepared by immersing vapor deposited gold substrates in a 30 millimolar solution of phenethylmercaptan (PEM) [$C_6H_5CH_2CH_2SH$] in ethanol in accordance with Nuzzo et al., *J. Am. Chem. Soc.,* 109, 733 (1987). The gold substrates were kept in solution for at least five days prior to use and rinsed with ethanol before introduction into the ultra high voltage (UHV) analysis chamber. Thiols adsorb to gold by a strong S-Au bond and are stable in air and vacuum.

The SAMs were analyzed using a mass spectrometric system as disclosed in U.S. Pat. No. 5,272,338. Molecules desorbed by 8 keV, 1 $\mu$s pulse of $Ar^+$ or $H_2^+$ were ionized using a 6 ns pulsed laser beam of 266 nm photons (3 mJ/pulse) located approximately 1 cm above the surface. The density of molecules in the laser plane was recorded as a function of time by varying the delay between the primary ion beam impact and the laser pulse. Analysis of the ionized particles was achieved by time-of-flight mass spectrometry using a gated detector to select the ion of interest. The distribution of flight times from the surface to the laser was recorded while monitoring m/z 105 [$C_6H_5CH_2CH_2^+$], which was the most abundant ion in the mass spectrum. No molecular ion was observed during sputtering or during a gas phase multiphoton ionization (MPI) in which PEM vapor was introduced into the chamber. A detailed description of the apparatus used is provided in Kobrin et al., *Rev. Sci. Inst.,* 57, 1354 (1986).

Figure 2:
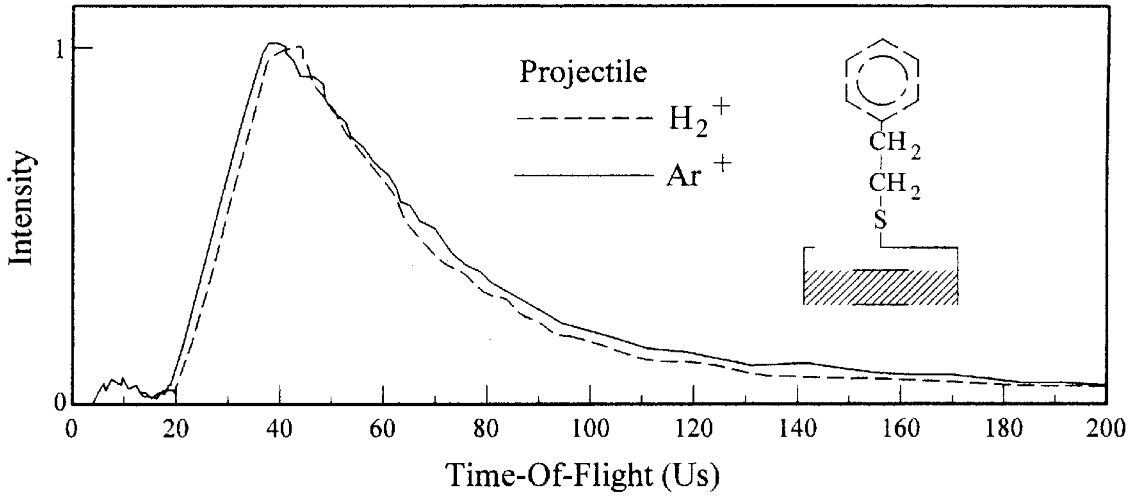
FIG. 2 is a graph depicting time-of-flight distributions of intensity (y-axis) over time-of-flight ($\mu$s; x-axis) of phenethylmercaptan subsequent to impact of $H_2^+$ and $Ar^+$.
Figure 3:
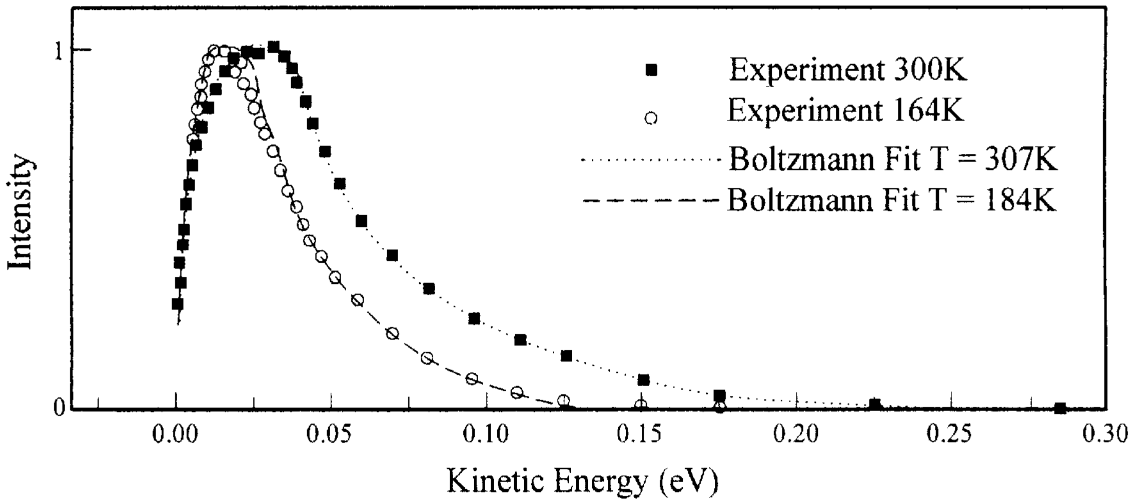
FIG. 3 is a graph depicting kinetic energy distributions of intensity (y-axis) over kinetic energy (eV; x-axis) of phenethylmercaptan at 300 K and 184 K, shown with corresponding Maxwell-Boltzmann fit.

Time-of-flight distributions for phenethylmercatpan desorbed upon bombardment with $Ar^+$ and $H_2^+$ are displayed in FIG. 2, in which the y-axis is labeled Intensity and the x-axis is labeled Time-of-Flight ($\mu$s). The shape of the distributions obtained using both $Ar^+$ and $H_2^+$ projectiles are nearly identical in the region between 20 and 200 $\mu$s and the most probable time to traverse the distance from the surface to the photon field is 35 $\mu$s. The corresponding kinetic energy distribution (flux) for the $H_2^+$ projectile is represented by the solid points in FIG. 3, in which the y-axis is labeled Intensity and the x-axis is labeled Kinetic Energy (eV). This curve indicates that the desorbed molecules have thermal translational energies (ca. 0.025 eV) and have been fit by a Maxwell-Boltzmann distribution at room temperature using standard methods. Cooling the sample to 165 K causes a marked shift to lower energy, which is again described by a Maxwell-Boltzmann distribution. The dependence of the desorbed molecule kinetic energy on substrate temperature was observed for both projectiles. The time-of-flight axis was transformed to kinetic energy under the assumption that [$C_6H_5CH_2CH_2$] (105 amu) was the molecule desorbed from the surface. It is possible that the entire PEM molecule was desorbed and that photofragmentation to form m/z 105 occurred during the ionization process. Such a scenario would cause a shift toward a slightly higher kinetic energies, however, the trends observed as a function of surface temperature would still hold.

Figure 4:
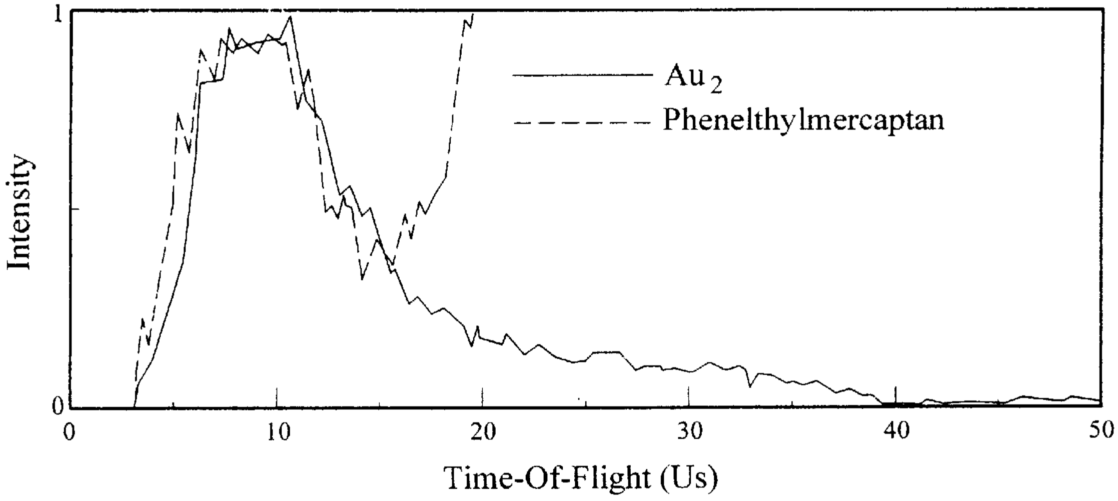
FIG. 4 is a graph depicting time-of-flight distributions of intensity (y-axis) over time-of-flight ($\mu$s; x-axis) of gold-dimer shown with the high energy component of phenethylmercaptan.

A peak centered at approximately 7 $\mu$s is evident in the PEM time-of-flight distribution produced by the $Ar^+$ projectile (FIG. 2). This peak has nearly the same position in time as that of the sputtered gold dimer (FIG. 4, labeled Intensity on the y-axis and Time-of-Flight ($\mu$s) on the x-axis), indicating that the molecules in the high energy component of the PEM distribution have velocities nearly identical to that of sputtered $Au_2$. No gold signal was observed while using $H_2^+$ as a projectile.

Almost all of the desorbed molecules leave the surface with thermal kinetic energies. This result is surprising in view of the fact that the PEM molecules are bound to the surface through a S—Au bond estimated to have an energy of 2 eV (Kobrin et al. supra). This observation is consistent with the presumption that the energy imparted to the gold substrate has no effect on the low energy, high intensity portion of the time-of-flight distribution, which is indicated because the distribution profile is independent of projectile mass.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for identifying an unknown molecule bound to a substrate in a substrate-linking moiety-unknown molecule complex, comprising the steps of:

(a) providing a substrate-linking moiety-unknown molecule complex comprising (i) a substrate bound to a plurality of sulfur linking moieties by a plurality of S—Au bonds and (ii) a plurality of unknown molecules bound to the plurality of linking moieties by a plurality of S—C bonds;

(b) bombarding the complex with focused energized particles selected from the group consisting of Ar and $H_2$ ions to separate at least one of the unknown molecules from the complex; and (c) determining the molecular weight of the at least one of the unknown molecules separated from the complex by time of flight secondary ion mass spectrometry.

2. The method of claim 1, further comprising the step of irradiating the at least one of the unknown molecules separated from the complex with photons.

3. The method of claim 1, wherein the plurality of unknown molecules comprises $CH_2CH_2C_6H_5$.

4. The method of claim 1, wherein the substrate is shaped into a bead.

5. The method of claim 4, wherein the bead has a diameter of from about 10 microns to about 120 microns.

6. The method of claim 1, wherein the particles are energized by subjection to an accelerating potential of between about one to about 30 kilovolts.

7. The method of claim 1, wherein the particles are energized by subjection to an accelerating potential of about eight kilovolts.

* * * * *